United States Patent
Koller

(10) Patent No.: US 8,789,713 B2
(45) Date of Patent: Jul. 29, 2014

(54) SURGICAL INSTRUMENT CADDY

(76) Inventor: Charles Koller, Winter Park, FL (US)

( * ) Notice: Subject to any disclaimer, the term of this patent is extended or adjusted under 35 U.S.C. 154(b) by 0 days.

(21) Appl. No.: 13/555,788

(22) Filed: Jul. 23, 2012

(65) Prior Publication Data
US 2014/0021079 A1 Jan. 23, 2014

(51) Int. Cl.
 *A47F 7/00* (2006.01)
 *A47G 29/00* (2006.01)
 *B01L 9/06* (2006.01)
 *A61B 19/02* (2006.01)

(52) U.S. Cl.
 CPC ............. *B01L 9/06* (2013.01); *A47F 7/0028* (2013.01); *A61B 19/0256* (2013.01); *A61B 19/02* (2013.01)
 USPC ...... 211/85.13; 211/85.18; 211/74; 211/70.6; 206/370

(58) Field of Classification Search
 CPC ............ B25H 3/003; B25H 3/02; B25H 3/04; B25H 3/06; A61C 3/04; A47F 7/0028; A47F 7/0035; A47F 7/0021; A47F 7/28; A47F 7/283; B01L 9/06; B01L 9/54; B01L 9/543; B01L 9/00; B43K 23/001; B43K 23/002; A47B 96/1408; A47B 96/1458; A47B 73/00; A47B 81/007; A61B 19/0256; A61B 2019/0258; A61B 2019/0259; A61B 19/02; F17C 13/084; B65D 85/20; B65D 85/42
 USPC ............ 211/69, 69.1, 107, 13.1, 65, 66, 70.6, 211/60.1, 85.13, 85.18, 196, 205, 69.5, 211/70.8, 70.2, 74, 75; 422/560, 562, 561, 422/566; 206/446, 305, 363–370, 373, 438, 206/376; 269/3, 6, 71, 95, 900; 248/689, 248/316.1, 313, 314
 See application file for complete search history.

(56) References Cited

U.S. PATENT DOCUMENTS

| | | | | | |
|---|---|---|---|---|---|
| 1,795,296 | A | * | 3/1931 | De Zeng | 248/157 |
| 2,429,305 | A | * | 10/1947 | Barnes | 211/69 |
| 2,587,921 | A | * | 3/1952 | Suite | 42/71.01 |
| 3,431,041 | A | * | 3/1969 | Fontlladosa | 312/284 |
| 3,612,336 | A | * | 10/1971 | Wilkich | 220/516 |
| 4,190,166 | A | * | 2/1980 | Allsop | 211/60.1 |
| 4,253,830 | A | * | 3/1981 | Kazen et al. | 433/77 |
| 4,397,395 | A | * | 8/1983 | McKelvey | 211/69 |
| 4,938,369 | A | * | 7/1990 | Carilli | 211/74 |
| 4,971,271 | A | * | 11/1990 | Sularz | 248/68.1 |
| 5,098,235 | A | * | 3/1992 | Svetlik et al. | 408/234 |
| 5,148,919 | A | * | 9/1992 | Rubin | 206/443 |
| 5,188,242 | A | * | 2/1993 | Smith | 211/69 |
| 5,288,093 | A | * | 2/1994 | Gross | 280/292 |
| 5,316,246 | A | * | 5/1994 | Scott et al. | 248/68.1 |
| 5,319,816 | A | * | 6/1994 | Ruehl | 5/600 |
| 5,447,243 | A | * | 9/1995 | Graber | 211/69.5 |
| 5,485,931 | A | * | 1/1996 | Barr, Jr. | 211/70.6 |
| D372,092 | S | * | 7/1996 | Brown, II | D24/128 |
| 5,655,741 | A | * | 8/1997 | Watkins | 248/289.11 |
| 5,850,917 | A | * | 12/1998 | Denton et al. | 206/366 |

(Continued)

*Primary Examiner* — Jennifer E Novosad
(74) *Attorney, Agent, or Firm* — Jason T. Daniel, Esq.; Daniel Law Offices, P.A.

(57) ABSTRACT

A surgical instrument caddy includes an elongated, generally rectangular main body having a support rod secured to one end and a plurality of hollow channels disposed therein. Each of the channels includes a first end terminating at the top surface of the main body, and a second end terminating at the bottom surface of the main body.

15 Claims, 5 Drawing Sheets

(56) References Cited

U.S. PATENT DOCUMENTS

| | | | |
|---|---|---|---|
| 5,906,284 A * | 5/1999 | Hammerstrom et al. | 211/205 |
| 5,992,912 A * | 11/1999 | Zimm | 294/143 |
| 6,349,827 B1 * | 2/2002 | Feder | 206/373 |
| 6,390,311 B1 * | 5/2002 | Belokin | 211/204 |
| 7,036,668 B2 * | 5/2006 | Udy | 211/70.6 |
| 7,506,775 B2 * | 3/2009 | Hartzell et al. | 220/1.5 |
| 7,591,616 B1 * | 9/2009 | Kerner | 408/124 |
| 7,959,014 B2 * | 6/2011 | Dredla, IV | 211/13.1 |
| 7,987,983 B1 * | 8/2011 | Guitreau | 206/443 |
| 2003/0161764 A1 * | 8/2003 | Itoh | 422/104 |
| 2003/0178331 A1 * | 9/2003 | Roberts | 206/315.1 |
| 2006/0278785 A1 * | 12/2006 | Wiesner et al. | 248/231.71 |
| 2013/0112636 A1 * | 5/2013 | Williams-Shelton et al. | 211/85.13 |

* cited by examiner

SURGICAL INSTRUMENT CADDY

TECHNICAL FIELD

The present invention relates generally to medical type devices, and more particularly to a surgical instrument caddy for holding laparoscopic instruments during a surgical procedure.

BACKGROUND

The statements in this section merely provide background information related to the present disclosure and may not constitute prior art.

Side tables for positioning traditional surgical instruments such as scalpels, clamps, retractors, dilators, suction tips, scopes and probes, for example, are well known in the art and typically include a free standing platform having a flat surface onto which these items can be placed during an operation.

In recent years, scientific advancements have allowed an ever increasing number of surgical procedures to be performed utilizing minimally invasive techniques. The most common form of minimally invasive surgery in the United States is laparoscopic surgery in which a surgeon makes one or more small incisions in the abdomen of a patient and then utilizes a thin, lighted tube to access the abdominal cavity.

Special laparoscopic instruments such as cannulas, trocars, sealers, cutters and the like are elongated and delicate instruments which must remain sterile at all times. Although there are known devices that can assist a surgeon by maintaining the position of a single laparoscopic instrument that is in direct contact with a patient, there is no such device that can store and position a plurality of laparoscopic instruments that are not actively being used. Moreover, owing to the size and shape of laparoscopic devices, traditional surgical tables are not ideally suited to for these types of instruments. As a result, it is common practice for surgeons to place the laparoscopic instruments on the actual patient and/or the patient's bed during the procedure. This practice is not ideal, as involuntary movements by the patient and/or the surgeon often causes the instruments to fall to the floor. When this occurs, the delicate laparoscopic instrument can become damaged and must be inspected and then re sterilized before it can be used again.

Accordingly, the need exists for a surgical instrument caddy that can position any number of laparoscopic instruments at a convenient location for a surgeon that does not suffer from the drawbacks described above.

SUMMARY OF THE INVENTION

The present invention is directed to a surgical instrument caddy. One embodiment of the present invention can include an elongated, generally rectangular main body having a support rod secured to one end, and a plurality of hollow channels disposed therein. Each of the channels can include a first end terminating at the top surface of the main body, and a second end terminating at the bottom surface of the main body, in order to receive a surgical instrument.

Another embodiment of the present invention can include one or more removable sleeves capable of being secured within the channels in order to receive surgical instruments.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

FIG. 4a is a partial cutout view of the surgical instrument caddy in accordance with the other embodiment.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Although described throughout this document as for use with laparoscopic surgical instruments, this is for illustrative purposes only, as those skilled in the art will recognize that the device 10 can be utilized for any number of different types of medical instruments. For purposes of this description, the terms "upper," "bottom," "right," "left," "front," "vertical," "horizontal," and derivatives thereof shall relate to the invention as oriented in FIG. 1.

Figure 1:
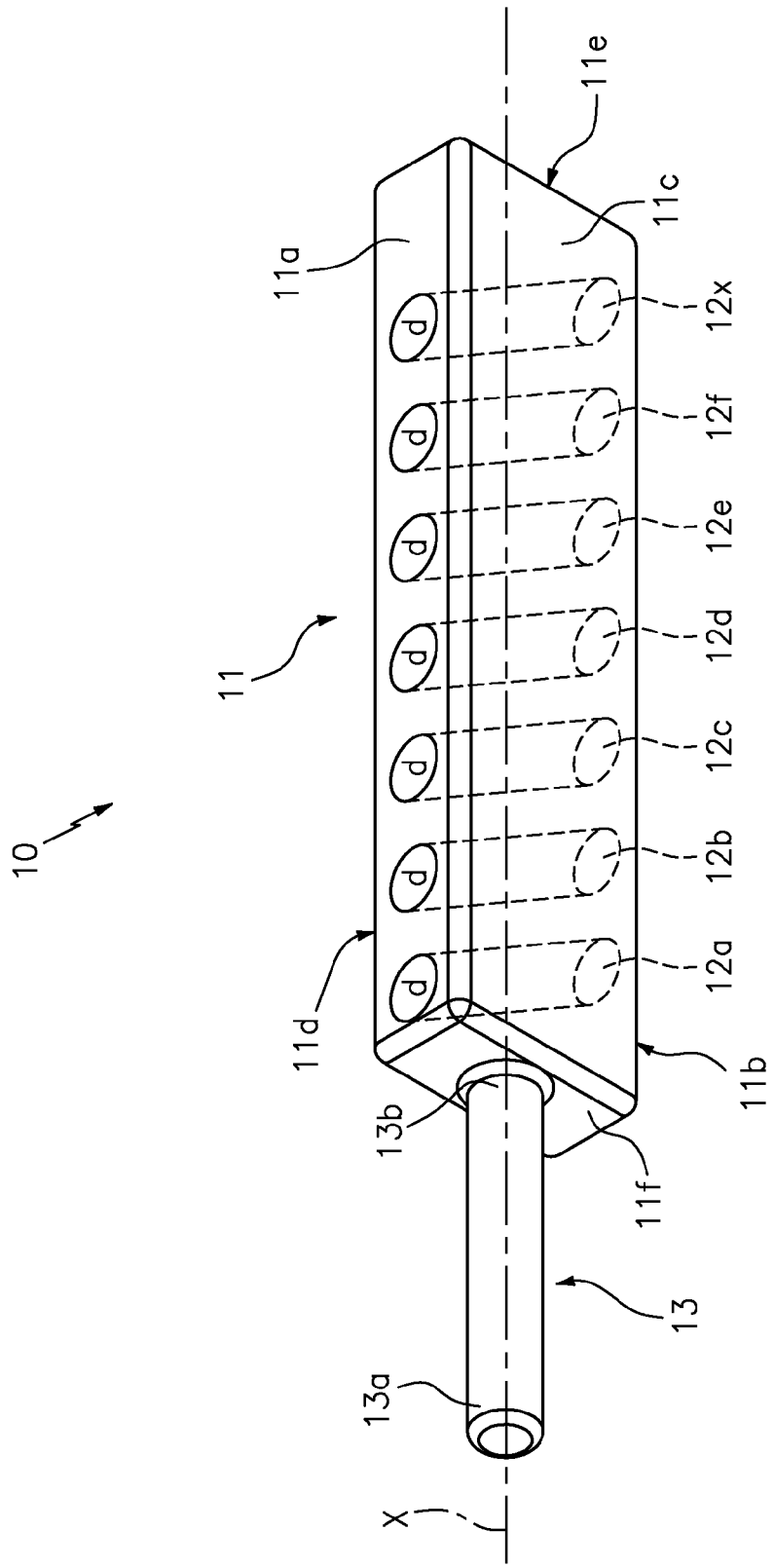
FIG. 1 is a perspective view of a surgical instrument caddy that is useful for understanding the inventive concepts disclosed herein.
Figure 2:
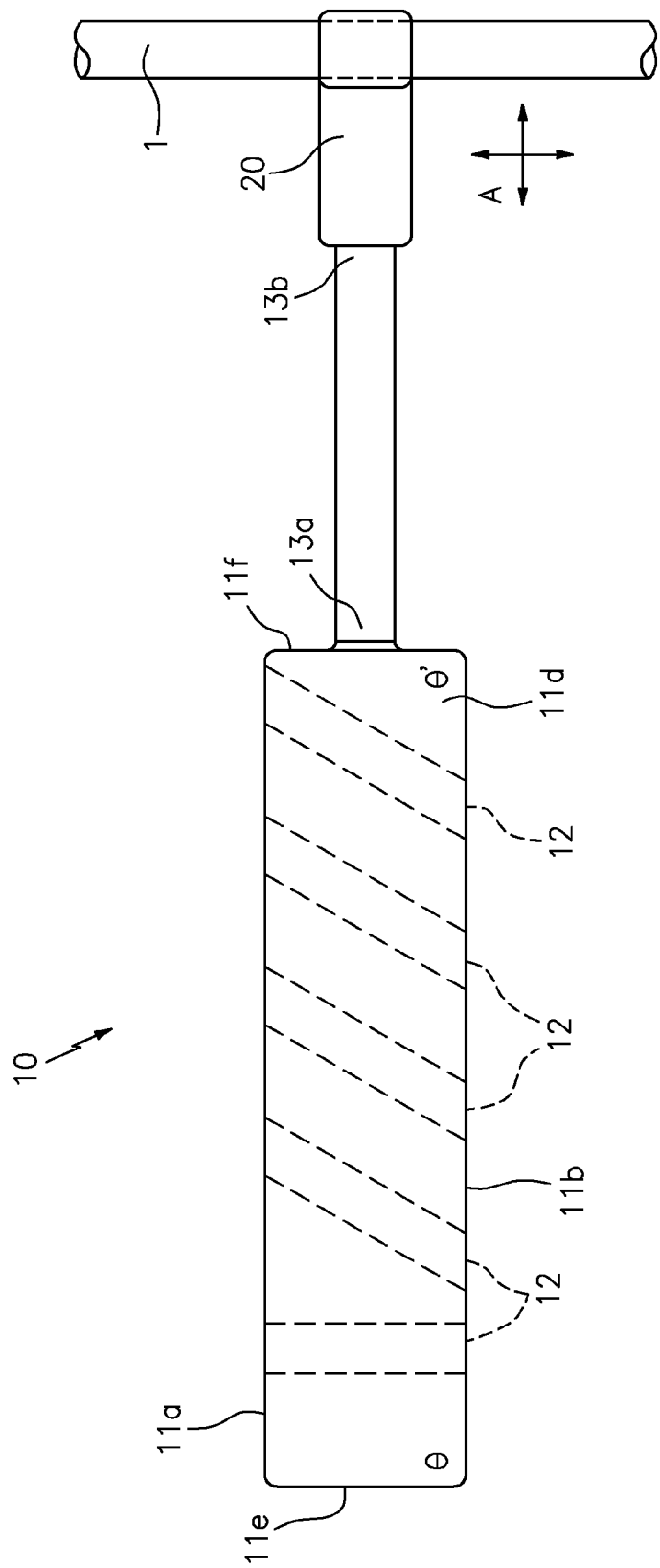
FIG. 2 is a side view of the surgical instrument caddy in accordance with one embodiment of the invention.

FIGS. 1 and 2 illustrate one embodiment of a surgical instrument caddy that is useful for understanding the inventive concepts disclosed herein. As shown, the caddy 10 can include a main body 11, a plurality of openings 12 and a connection rod 13.

The main body 11 can preferably be constructed from a single piece of cast aluminum forming an elongated, generally rectangular shape. The shape can include a top surface 11a, a bottom surface 11b, a pair of opposing side surfaces 11c, and 11d, and a pair of opposing end surfaces 11e and 11f.

Although described above as including a rectangular shape and aluminum construction material, this is for illustrative purposes only. To this end, the main body can take any number of conventional shapes and can be made from any number of construction materials such as steel and plastic, among many others, for example.

A plurality of channels 12a-12x can be positioned throughout the main body 11. Each of these channels 12 can form a hollow pathway extending from the top surface of the main body 11a through the bottom surface of the main body 11b. Each of the channels 12 can include an inside dimension d suitable for receiving a laparoscopic instrument and securely positioning the same for use during a surgical procedure. In one preferred embodiment, each of the channels 12 can be positioned at an angle θ of between approximately 33° and 45° with respect to the X axis, however, any number of other angles are also contemplated. Moreover, each of the channels 12 can be disposed at identical angles, or one of more channels can be disposed at a different angle θ', as shown in FIG. 2.

As described herein, each of the channels 12 can be integrated into the construction the main body either through molding or casting, or can be drilled into an already formed main body material. The dimension d of each of the channels 12a-12x will preferably range from approximately 10 mm to 25 mm. To this end, the channels 12a-12x can include a dimension d that is identical to the other channels, or can include a dimension d that is different from the other channels. Such a feature can act to allow the device to receive a standardized sleeve 30, as will be described below, or to directly receive laparoscopic instruments having varying widths and dimensions.

An elongated, generally tubular support rod 13 can act to position the main body in accordance with the preferences of a user. The support rod can include a first end 13a and a second end 13b that is secured to the end of the main body 11f. In one preferred embodiment, the support rod 13 can be integrated into the construction of the main body through molding or casting, and will therefore be constructed from an identical material as that of the main body. Alternatively, the support rod can be constructed from any number of sturdy materials such as steel, for example, that is permanently affixed to the main body via a traditional method such as welds, bolts or other known techniques. In either instance, it is preferred that the entire device 10 be constructed from generally nonporous materials which allow for easy sterilization within operating room facilities.

As shown in FIG. 2, the device 10 can further include an optional clip/connector 20 disposed along the first end of the support rod 13a. The connector 20, can preferably act to removably secure the device in an omnidirectional manner (See arrow A) to a variety of equipment 1 that is commonly found in an operating room. In one preferred embodiment, the connector 20 can comprise a ball joint fastener such as that described in U.S. Pat. No. 4,571,110, however any number of conventionally known and commercially available clamps or fasteners can also be utilized herein.

While the dimensions of the elements are not critical, in the preferred embodiment the main body can include a length (X axis) of approximately 21 inches, a width (11c to 11d) of approximately 1.5 inches, and a depth (11a to 11b) of approximately 3 inches Likewise, the support rod can preferably include a length (X axis) of approximately 6 inches and a thickness of approximately 1 inch.

Figure 3:
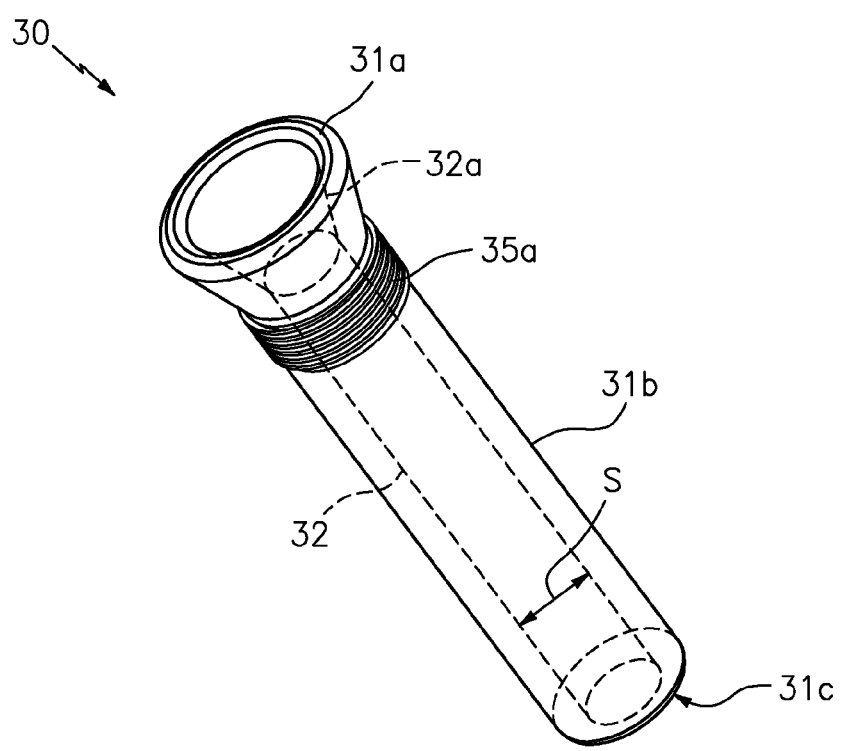
FIG. 3 is a perspective view of a removable sleeve for use with the surgical instrument caddy in accordance with one embodiment.

FIG. 3 illustrates one embodiment of a removable sleeve 30 which can be utilized with the surgical instrument caddy 10. As described below, the sleeve 30 can be inserted into, and retained within the channels 12 of the main body. As such, each sleeve 30 can include a generally tubular main body 31 having a top portion 31a, a middle portion 31b and a bottom portion 31c. A hollow sleeve channel 32 can extend from the top portion 31a to the bottom portion 31c. The sleeve channel can include a funnel shaped area 32a along the upper portion in order to guide a laparoscopic instrument into the sleeve channel.

The sleeve channel 32 can preferably include an inside dimension S of between approximately 8 mm and 14 mm. As is known to those of skill in the art, conventional laparoscopic instruments are typically constructed to include an outside dimension of between 5 mm and 12 mm. As such, the inside dimension s of the sleeve channel 32 is slightly larger than the dimension of the laparoscopic instrument. Such a feature can allow the removable sleeve 30 to act as a cradle for storing the instrument with the caddy.

The removable sleeve 30 can also include a plurality of threaded elements 35a that are disposed along the outside portion of the main body 31, in order to allow the sleeve to be securely yet removably fastened within the channels 12, as will be described below.

Figure 4:
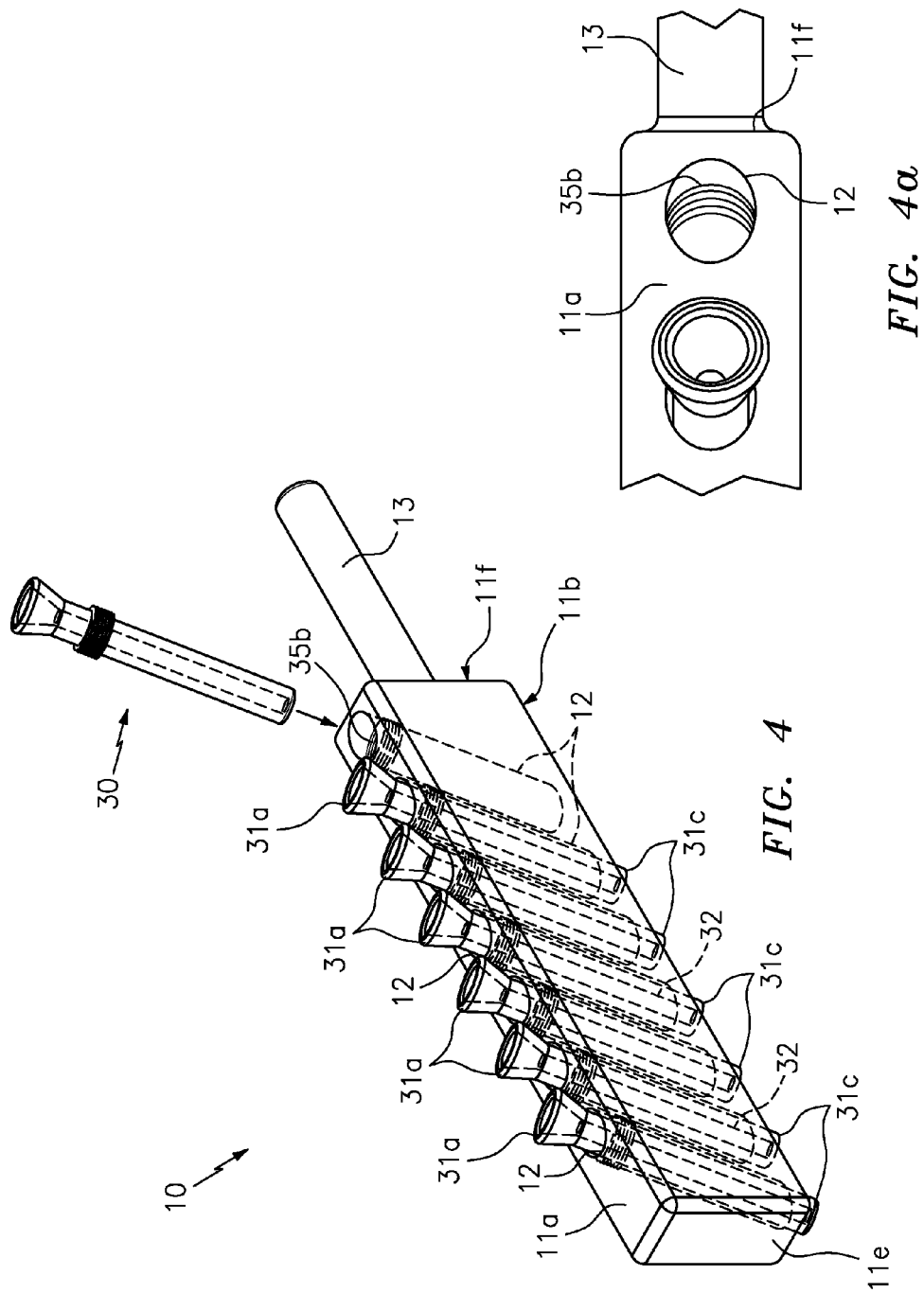
FIG. 4 is a perspective view of the surgical instrument caddy in accordance with another embodiment of the invention.

FIG. 4 illustrates an alternate embodiment of the surgical instrument caddy 10 that further includes a plurality of embedded screw threads 35b for mating with threads 35a of a removable sleeve 30. In one preferred embodiment, threads 35b can be located along the upper portion of each of the channels 12 at a location that is adjacent to the top surface 11a. As shown, threaded elements 35a and 35b can act to removably secure a single sleeve 30 within a single channel 12. Threaded elements for securing complementary objects together via a twisting motion are extremely well known in the art, and no further description is deemed necessary.

Although described above as including threaded elements, one of skill in the art will recognize that other conventional devices for removably securing objects together can also be utilized herein without undue experimentation. Several non-limiting examples include opposing magnetic elements disposed on the sleeve and the channel, strips of hook and loop material as well as conventional compression fittings, among many others. Accordingly, the inventive concepts are not to be construed as limited to the use of threaded elements.

By providing a plurality of removable sleeves 30 each including an inner channel 32 having a dimension S for specifically receiving a laparoscopic instrument having a known size, the inventive concepts disclosed herein can allow a single main body to be constructed having a plurality of channels 12 with an identical dimension size d in order to receive the removable sleeves. Moreover, as each of the sleeves can include different internal dimensions s for positioning different laparoscopic instruments, the presently claimed invention can allow a user to customize the device for a particular surgery. Further, as only the sleeves 30 will be in direct contact with the surgical instruments, it may only be necessary to sterilize the sleeves 30 after each procedure, as opposed to requiring the entire device 10 to be sterilized. Such a feature can result in a substantial financial savings over the life of the product.

Figure 5:
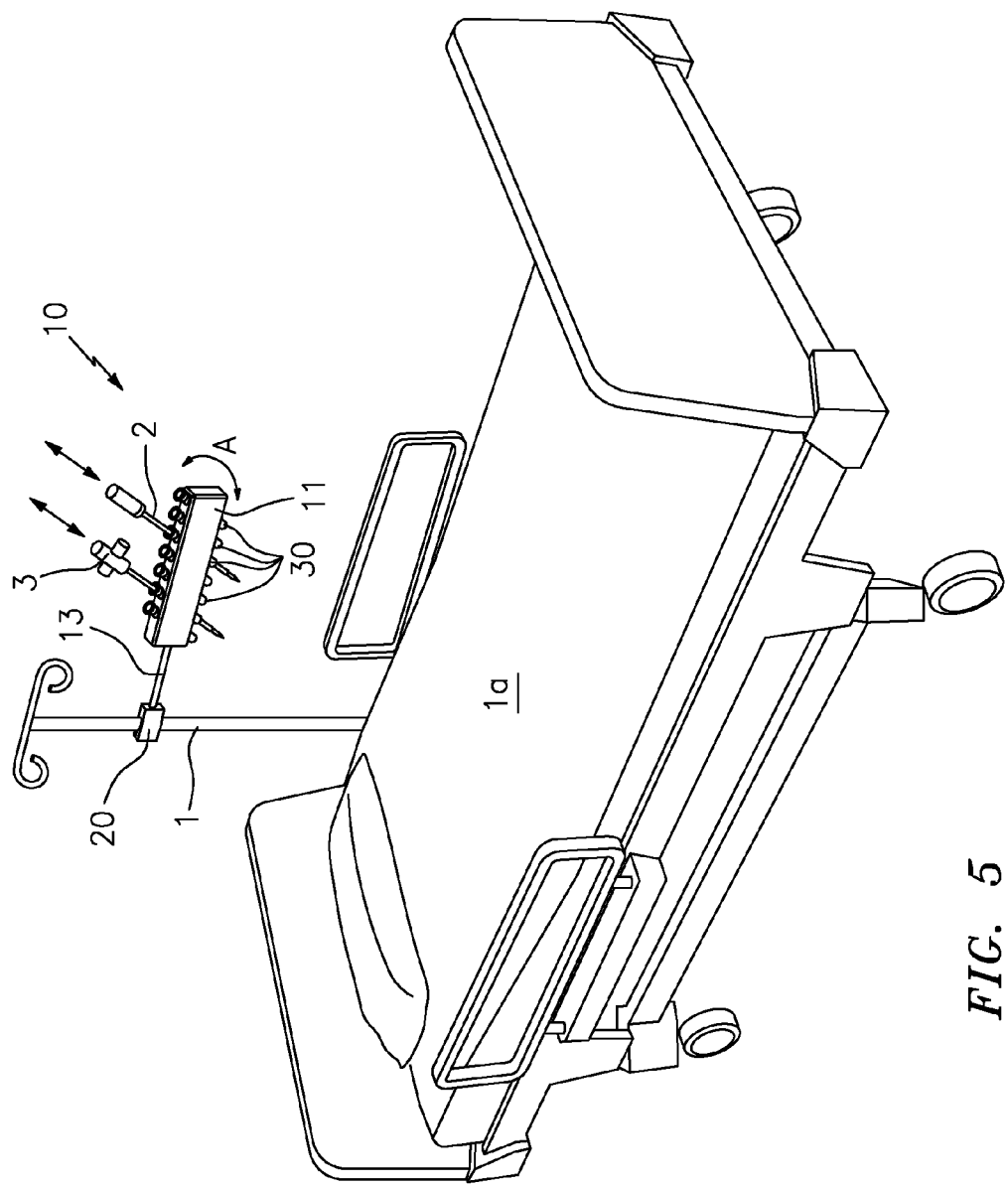
FIG. 5 is a perspective view of the surgical instrument caddy in operation.

FIG. 5 illustrates one embodiment of the surgical instrument caddy 10 in operation. As shown, the device 10 can be secured to a piece of operating room equipment 1, such as the vertical IV rail of a hospital bed 1a, for example via the connector 20. Next, a plurality of sleeves 30 can be secured within the main body in order to receive various types of laparoscopic equipment, such as a cannula 2 and a trocar 3. When so arranged, the caddy 10 can act as a stable, sanitary platform for holding laparoscopic instruments that prevents the need to rest the instruments on the patient or the patient bed.

As described herein, one or more elements of the surgical instrument caddy 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individual elements such as main body 11, channels 12 and/or support rod 13, for example, may be formed together as one continuous element, either through manufacturing processes, such as welding, casting, or molding, or through the use of a singular piece of material milled or machined with the aforementioned components forming identifiable sections thereof. Accordingly, in one alternate embodiment, each of the above described elements 11-13 of the caddy 10 can be constructed from a single mold of injected plastic; however other materials such as metal and rigid plastic are also contemplated.

As described above, dimensions d and s are intended to represent lateral space such as the width along the X axis and/or the diameter of the openings.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A surgical instrument caddy, comprising:
   an elongated, generally rectangular main body having a top surface, a bottom surface, first and second side surfaces and first and second end surfaces;
   an elongated, generally tubular support rod having a first and second end, said first end being permanently affixed to the first end surface of the main body;
   a plurality of channels disposed within the main body, each of said channels having a first end terminating at the top surface of the main body, and a second end terminating at the bottom surface of the main body, each of said channels further including a plurality of threaded elements that are disposed along the first end thereof; and
   one or more removable sleeves that are configured to be positioned within one of the plurality of channels, each of said sleeves including a generally tubular body having a top end, a bottom end and a sleeve channel extending from the top end through the bottom end,
   each of the one or more removable sleeves further including a plurality of complementary threaded elements that are disposed along the top end of the sleeve body, said complementary threaded elements functioning to engage the threaded elements of one of the plurality of channels.

2. The instrument caddy of claim 1, wherein each of the plurality of channels are positioned at an angle with respect to the top surface and the bottom surface.

3. The instrument caddy of claim 2, wherein said angle includes a range of between 33 degrees and 45 degrees.

4. The instrument caddy of claim 2, wherein the angle of each of the plurality of channels is identical.

5. The instrument caddy of claim 2, wherein the angle of at least one of the plurality of channels is different than the angle of another of the plurality of channels.

6. The instrument caddy of claim 1, wherein a dimension of each of the plurality of channels includes a width of between 10 millimeters and 25 millimeters.

7. The instrument caddy of claim 6, wherein each of the channels includes an identical sized dimension.

8. The instrument caddy of claim 6, wherein at least one of the plurality of channels includes a dimension that is not the same as the dimension of another of the plurality of channels.

9. The instrument caddy of claim 1, wherein each of the main body and the support rod are constructed from a nonporous material configured to be sterilized within an operating room facility.

10. The instrument caddy of claim 1, further comprising:
    a connector that is in communication with the support rod, said connector being configured to removably secure the caddy to an external object.

11. The instrument caddy of claim 10, wherein said connector is omnidirectional, and is configured to allow the caddy to be positioned at a plurality of different orientations.

12. The instrument caddy of claim 1, wherein the sleeve channel of each of the removable sleeves includes a dimension that is suitable for receiving a laparoscopic instrument.

13. The instrument caddy of claim 12, wherein the top end of each of the at least one removable sleeve includes a generally funnel shaped portion.

14. The instrument caddy of claim 12, wherein the sleeve channel of each of the one or more removable sleeves includes an identical sized dimension.

15. The instrument caddy of claim 12, wherein at least one of the sleeve channels of one of the removable sleeves includes a dimension that is different than the dimension of the sleeve channel of another of the one or more sleeves.

* * * * *